United States Patent [19]

Hyson

[11] Patent Number: 4,936,900

[45] Date of Patent: Jun. 26, 1990

[54] STABILIZED AQUEOUS FORMULATIONS OF SULFONYLUREA SALTS

[75] Inventor: Archibald M. Hyson, Landenberg, Pa.

[73] Assignee: E. I. du Pont de Nemours and Company, Wilmington, Del.

[21] Appl. No.: 1,336

[22] Filed: Jan. 7, 1987

Related U.S. Application Data

[63] Continuation of Ser. No. 581,118, Feb. 24, 1984, abandoned, which is a continuation-in-part of Ser. No. 482,025, Apr. 4, 1983, abandoned.

[51] Int. Cl.$^5$ .............. A01N 43/66; A01N 43/54; A01N 25/02; A01N 25/22
[52] U.S. Cl. ................................. 71/90; 71/92; 71/93; 71/DIG. 1
[58] Field of Search .............. 71/DIG. 1, 65, 81, 82, 71/90, 92, 93, 98, 113

[56] References Cited

U.S. PATENT DOCUMENTS

| | | | |
|---|---|---|---|
| 3,031,290 | 4/1962 | Senior | 71/65 |
| 3,152,879 | 10/1964 | Yale, Jr. | 71/65 |
| 4,394,506 | 7/1983 | Levitz | 544/321 |
| 4,552,582 | 11/1985 | Kruger | 71/73 |

OTHER PUBLICATIONS

Japn. Kokai, 7850-327, Chem. Abst., vol. 89. (1978), 101930w and Index Entry, p. 496, 10th Coll. Index.

Primary Examiner—Glennon H. Hollrah
Assistant Examiner—K. Konstas
Attorney, Agent, or Firm—Samuel S. Blight

[57] ABSTRACT

This invention relates to stabilized aqueous compositions consisting essentially of a sulfonylurea or its agriculturally suitable salt with a salt of a carboxylic or an inorganic acid, or with mixtures of such carboxylic or inorganic acid salts, provided that the solubility of carboxylic or inorganic acid salts at 5° C. and a pH of about 6-10 is greater than or equal to 3% and further provided that the pH of a 0.1 molar solution of the carboxylic or inorganic acid salt is between 6 and 10.

25 Claims, No Drawings

4,936,900

STABILIZED AQUEOUS FORMULATIONS OF SULFONYLUREA SALTS

This is a continuation of application Ser. No. 581,118 filed Feb. 24, 1984, which, in turn, is a continuation-in-part of application Ser. No. 482,025, filed Apr. 4, 1983, both now abandoned.

BACKGROUND OF THE INVENTION

This invention relates to stabilized aqueous compositions consisting essentially of a sulfonylurea or its agriculturally suitable salt with an effective amount of a salt of a carboxylic or an inorganic acid, or with mixtures of such carboxylic or inorganic acid salts, provided that the solubility of carboxylic or inorganic acid salts at 5° C. and a pH of about 6–10 is greater than or equal to 3% and further provided that the pH of a 0.1 molar solution of the carboxylic or inorganic acid salt is between 6 and 10.

Sulfonylureas, are known in the literature. For instance, U.S. Pat. Nos. 4,127,405 and 4,169,719 teach herbicidal sulfonylureas. The aqueous suspension formulations of these herbicides are stabilized by the technique of the instant invention.

The above-mentioned patents and others disclose sulfonylureas which are highly effective as herbicides. There is however, a need to store agriculturally suitable formulations of such sulfonylureas for long periods of time after they are produced. Maintaining the stability of formulations of such herbicides is extremely important since an unstable formulation will be considerably less effective when utilized. That is to say, the active ingredient must be maintained intact in the formulation if herbicidal effect is to be maximized.

According to the instant invention, a formulation has been discovered, described below, which serves to maintain the stability of sulfonylurea herbicides.

SUMMARY OF THE INVENTION

This invention relates to a stabilized aqueous suspension composition consisting essentially of a compound of Formula I or its agriculturally suitable of Formula II with an effective amount of a salt of a carboxylic or an inorganic acid, or with mixtures of such carboxylic or inorganic acid salts, provided that the solubility of carboxylic or inorganic acid salts at 5° C. and at pH 6–10 is greater than or equal 3% and further provided that the pH of a 0.1 molar aqueous solution of the carboxylic or inorganic acid salt is between 6 and 10. All parts are by weight unless otherwise indicated.

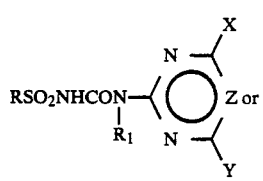

I

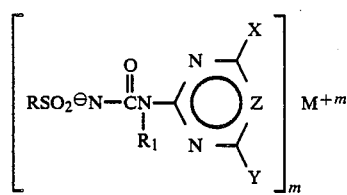

II

The concentration of the carboxylic or inorganic acid salt or salts in the composition is between 3% and the salt saturation limit of the aqueous solution. The values for the substituents are as follows:

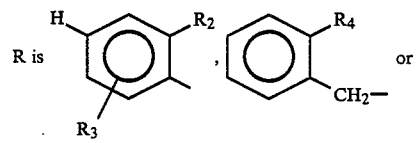

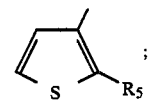

$R_1$ is H or $CH_3$;
$R_2$ is F, Cl, Br, $C_1$–$C_4$ alkyl, $SO_2NR_6R_7$, $S(O)_nR_8$, $SO_2NCH_3(OCH_3)$, $CO_2R_9$, $OSO_2R_{10}$, $OR_{11}$, $NO_2$,

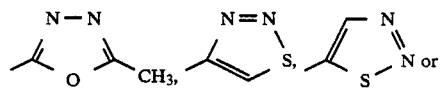

$R_3$ is H, F, Cl, Br, $CH_3$, $OCH_3$ or $CF_3$;
$R_4$ is Cl, $NO_2$ or $CO_2R_{10}$;
$R_5$ is Cl, Br, $SO_2NR_6R_7$, $S(O)_nR_{10}$ or $CO_2R_{10}$;
$R_6$ and $R_7$ are independently $C_1$–$C_3$ alkyl;
$R_8$ is $C_1$–$C_3$ alkyl or $C_1$–$C_3$ alkyl substituted by 1–5 atoms of F, Cl or Br;
$R_9$ is $C_1$–$C_4$ alkyl, $CH_2CH_2OCH_3$, $CH_2CH_2Cl$ or $CH_2CH=CH_2$;
$R_{10}$ is $C_1$–$C_3$ alkyl;
$R_{11}$ is $C_1$–$C_4$ alkyl, $CH_2CH=CH_2$, $CH_2C\equiv CH$, or $C_1$–$C_3$ alkyl substituted with 1–5 atoms of F, Cl or Br;
n is 0 or 2;
Z is CH or N;
X is $CH_3$, $OCH_3$, Cl or $OCHF_2$;
Y is $CH_3$, $OCH_3$, $CH(OCH_3)_2$, $OCHF_2$ or

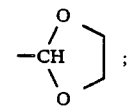

and
$M^{+m}$ is an agriculturally suitable cation; and
m is 1, 2, or 3;
provided that when X is Cl then Z is CH and Y is $OCH_3$ or $OCF_2H$.

The compositions of this invention may contain more than one compound of Formula I or more than one compound of Formula II. In addition, the compositions may contain compounds of both Formula I and Formula II, simultaneously. The compositions of this invention may also optionally contain other herbicides.

Preferred for reasons of their greater stability and/or their more favorable physical properties are:

(1) Compositions of the Generic Scope consisting of a compound of Formula I or a compound of Formula II wherein M is an ammonium, substituted ammonium or alkali metal ion and the counter ion of the carboxylic or inorganic acid salt is an ammonium, substituted ammonium or alkali metal ion.

(2) Compositions of the Preferred 1 wherein

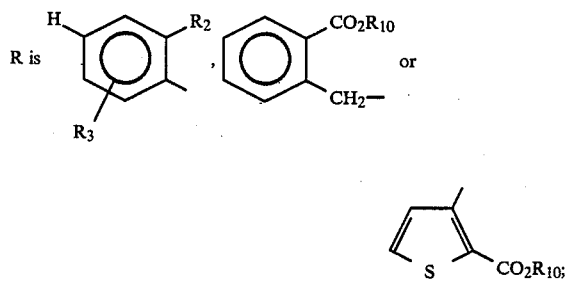

$R_1$ is H;
$R_2$ is Cl, $CH_3$, $SO_2N(CH_3)_2$, $S(O)_nR_8$, $CO_2R_9$, $OSO_2R_{10}$, $OR_{11}$ or $NO_2$;
$R_3$ is H, Cl, $CH_3$, $OCH_3$ or $CF_3$;
$R_8$ is $C_1-C_3$ alkyl, $CF_3$, $CF_2H$ or $CF_2CF_2H$;
$R_9$ is $C_1-C_4$ alkyl; and
$R_{11}$ is $C_1-C_4$ alkyl, $CF_3$, $CF_2H$ or $CF_2CF_2H$.

(3) Compositions of the Preferred 2 wherein the compound is an agriculturally suitable salt of Formula II.

(4) Compositions of the Preferred 3 wherein the cation of the compound of Formula II and the cation of the carboxylic or inorganic acid salt are identical.

(5) Compositions of the Generic Scope wherein the concentration of the carboxylic or inorganic acid salt or salts is greater than 10% and less than 40% or the salt saturation limit of the solution.

(6) Compositions of the Preferred 1 wherein the concentration of the carboxylic or inorganic acid salt or salts is greater than 10% and less than 40% or the salt saturation limit of the solution.

(7) Compositions of the Preferred 2 wherein the concentration of the carboxylic or inorganic acid salt or salts is greater than 10% and less than 40% or the salt saturation limit of the solution.

(8) Compositions of the Preferred 3 wherein the concentration of the carboxylic or inorganic acid salt or salts is greater than 10% and less than 40% or the salt saturation limit of the solution.

(9) Compositions of the Preferred 4 wherein the concentration of the caboxylic or inorganic acid salt or salts is greater than 10% and less than 40% of the salt saturation limit of the solution.

(10) Compositions of the Generic Scope wherein the salt or salts are selected from $C_1-C_3$ carboxylic acids and inorganic acid salts.

(11) Compositions of the Preferred 1 wherein the salt or salts are selected from $C_1-C_3$ carboxylic acids and inorganic acid salts.

(12) Compositions of the Preferred 2 wherein the salt or salts are selected from $C_1-C_3$ carboxylic acid s and inorganic acid salts.

(13) Compositions of the Preferred 3 wherein the salt or salts are selected from $C_1-C_3$ carboxylic acids and inorganic acid salts.

(14) Compositions of the Preferred 4 wherein the salt or salts are selected from $C_1-C_3$ carboxylic acids and inorganic acid salts.

Specifically preferred for reasons of their greatest stability and/or greatest utility are compositions containing compounds of Formula II selected from the agriculturally suitable salts of:

2-[[(4-chloro-6-methoxypyrimidin-2-yl)aminocarbonyl]aminosulfonyl]benzoic acid, ethyl ester;

2-[[(4-methoxy-6-methyl-1,3,5-triazin-2-yl)aminocarbonyl]aminosulfonyl]benzoic acid, methyl ester:

2-[[(4-6-dimethylpyrimidin-2-yl)aminocarbonyl]aminosulfonyl]benzoic acid, methyl ester;

2-chloro-N-[(4-methoxy-6-methyl-1,3,5-triazin-2-yl)aminocarbonyl]benzenesulfonamide;

2-[[(4,6-dimethoxypyrimidin-2-yl)aminocarbonyl]aminosulfonylmethyl]benzoic acid, methyl ester;

3-[[(4-methoxy-6-methyl-1,3,5-triazin-2-yl)aminocarbonyl]aminosulfonyl[-2-thiophenecarboxylic acid methyl ester;

N-[(4,6-dimethylpyrimidin-2-yl)aminocarbonyl]-2-hydroxybenzenesulfonamide, ethanesulfonate;

and compositions containing carboxylic or inorganic acid salts selected from:

diammonium hydrogen phosphate:
ammonium acetate:
lithium acetate;
sodium acetate:
potassium acetate: or
sodium thiocyanate;

and compositions containing:

the ammonium salt of 2-chloro-N-[(4-methoxy-6-methyl-1,3,5-triazin-2-yl) aminocarbonyl]benzene-sulfonamide and diammonium hydrogen phosphate.

DETAILED DESCRIPTION OF THE INVENTION

This invention relates to stable and readily dispersible concentrated liquid suspensions of compounds of Formula I or their agriculturally suitable salts of Formula II in aqueous salt solutions. Compounds of Formula I are useful herbicides and their preparation is known in the art. See, for example, U.S. Pat. Nos. 4,127,405 and 4,169,719. Agriculturally suitable salts of Formula II are also useful herbicides and can be prepared by a number of ways known to the art. For example, metal salts can be made by treating the compounds of Formula I with a solution of an alkali metal salt having a sufficiently basic anion (e.g., hydroxide, alkoxide carbonate or hydride). Ammonium and substituted ammonium salts can be made by similar techniques.

Salts of Formula II can also be prepared by exchange of one cation for another. Cationic exchange can be effected by direct treatment of an aqueous solution of a salt of Formula II (e.g.. alkali metal or ammonium salt) with a solution containing the cation to be exchanged. This method is most effective when the desired salt containing the exchanged cation is insoluble in water and can be separated by filtration.

Exchange may also be effected by passing an aqueous solution of a salt of Formula II (e.g.. an alkali metal or ammonium salt) through a column packed with a cation exchange resin containing the cation to be exchanged. In this method, the cation of the resin is exchanged for that of the original salt and the desired product is eluted from the column. This method is particularly useful when the desired salt is watersoluble.

Liquid concentrates are desirable because of the ease with which they can be measured, poured, handled or diluted in preparing aqueous slurries for spraying. Some of the compounds of Formula I and salts of Formula II do not have high solubility in water or other inexpensive solvents and moreover they are chemically unstable over long periods of time in many of these solvents. When dissolved in water alone, either partially or completely, hydrolysis and/or crystal growth can occur in storage so that stable solutions or suspensions cannot be formulated.

It has been found that stabilized aqueous suspensions of compounds of Formula I or salts of Formula II can be prepared when the aqueous suspending medium contains ammonium, substituted ammonium or alkali metal salts of a carboxylic acid or an inorganic acid or mixtures of such salts provided that the solubility of those salts at pH 6-10 is greater than or equal to 3% at 5° C. and further provided that the pH of a 0.1 molar aqueous solution of the carboxylic or inorganic acid salt is between 6 and 10.

The stabilization which is achieved with these compositions is evident in several ways. First, the chemical stability of the compounds of Formula I or the salts of Formula II in an aqueous suspension is markedly improved which allows formulation of such a suspension that is relatively stable in storage. Second, crystal growth of active ingredient is reduced and a controlled degree of flocculation is imparted to the particles of active herbicide which prevents formation of a hard-to-resuspend cake during storage. Third, the density of the suspending medium may be up to 30% higher than that of water which reduces the settling tendency of the suspended particles. Fourth, the dissolved salts act as an antifreeze which maintains the fluidity of the compositions at temperatures down to −6° C. and below.

Another advantage of these compositions is that, although the compounds of Formula I and the salts of Formula II are relatively insoluble in the suspending medium, when diluted with water in the spray tank they quickly and completely dissolve at the more dilute spray concentrations, provided the pH of the spray solution is about 7.0 or above.

The salts which are preferred in the aqueous medium are ammonium, substituted ammonium or alkali metal salts of a carboxylic or an inorganic acid which are soluble in water at 3% or more at 5° C. The useful concentration range is from 3% to the saturation point at 5° C. The preferred salts of the invention will further possess a pH between 6 and 10 for a 0.1 molar aqueous solution. Examples of these salts are diammonium hydrogen phosphate, ammonium acetate, lithium acetate, sodium thiocyanate, sodium acetate, potassium acetate, or compatible mixtures of these. Diammonium hydrogen phosphate and sodium acetate are preferred for compositions containing the ammonium and sodium salts, respectively, of the salts of Formula II. The useful pH range of these compositions is 6-10 although 7-9 is preferred. In most cases, the salts described above will automatically produce a formulation with the desired pH. The anion of the carboxylic or inorganic acid salt may act as an acid acceptor and generate, in situ, the salt of Formula II from its corresponding conjugate acid.

Utilizing this principle, one may prepare these compositions of the salts of Formula II directly from the conjugate acids of Formula I. If a higher or lower pH is desired, a small amount of acid or base can be added to the formulation. For example, with diammonium hydrogen phosphate, the pH can be lowered by addition of phosphoric acid or ammonium dihydrogen phosphate. The pH may be raised with ammonium hydroxide. The base or acid may have the same anion or cation as the salt but this is not a requirement.

The formulations of this invention contain about 1 to 50% (preferably 10 to 40%) of the compounds of Formula I or the salts of Formula II suspended in an aqueous solution which contains from 3% to the salt saturation amounts of an agriculturally suitable salt of a carboxylic or an inorganic acid or mixtures thereof as described aboVe. Preferred concentrations of these carboxylic or inorganic acid salts are in the range of about 10-40% in the aqueous phase. The formulation may also contain about 0.1% to 20% of surfactants. Higher ratios of surfactant to active ingredient are sometimes desirable and can be achieved by incorporation into the formulation or by tank mixing.

Among the surfactants used in these compositions are common wetting and dispersing agents such as trimethylnonyl polyethylene glycol ether, sodium alkylnaphthalenesulfonates, sodium alkylbenzenesulfonates, sodium dioctyl sulfosuccinate, sodium dodecyl sulfate, the ammonium and sodium salts of lignosulfonic acid and formaldehyde condensates of naphthalenesulfonic acid. More specific examples are sodium ligninsulfonate and ammonium ligninsulfonate.

Optionally, the formulations may also contain about 0.01-5.0% of thickening or suspending agents such as sodium carboxymethyl cellulose, polysaccharide gums, natural and refined smectite type clays and synthetic silicas.

The compositions of this invention may contain more than one compound of Formula I or more than one compound of Formula II. In addition, the compositions may contain compounds of both Formula I and Formula II, simultaneously. The compositions of this invention may also optionally contain other herbicides. The following herbicides are examples of materials which may be particularly useful in such combinations:

| Common Name | Chemical Name |
| --- | --- |
| acifluorfen | 5-[2-chloro-4-(trifluoromethyl)-phenoxy[-2-nitrobenzoic acid |
| alachlor | 2-chloro-2',6'-diethyl-N-(methoxymethyl)acetanilide |
| ametryn | 2-(ethylamino)-4-(isopropylamino)-6-methylthio)-s-triazine |
| amitrole | 3-amino-s-triazole |
| AMS | ammonium sulfamate |
| asulam | methyl sulfanilylcarbamate |
| atrazine | 2-chloro-4-(ethylamino)-6-(isopropylamino)-s-triazine |
| barban | 4-chloro-2-butynyl m-chlorocarbanilate |
| benefin | N-butyl-N-ethyl-α,α,α-trifluoro-2,6-dinitro-p-toluidine |
| bensulide | O,O-diisopropyl phosphorodithioate S-ester with N-(2-mercaptoethyl)-benzenesulfonamide |
| benzipram | 3,5-dimethyl-N-(1-methylethyl)-N-(phenylmethyl)benzamide |
| benzoylprop | N-benzoyl-N-(3,4-dichlorophenoxy)-DL-alaine |
| bifenox | methyl 5-(2,4-dichlorophenoxy)-2-nitrobenzoate |
| bromacil | 5-bromo-3-sec-butyl-6-methyluracil |

| Common Name | Chemical Name |
|---|---|
| bromoxynil | 3,5-dibromo-4-hydroxybenzonitrile |
| butachlor | N-(butoxymethyl)-2-chloro-2,',6'-diethylacetanilide |
| butam | 2,2-dimethyl-N-(1-methylethyl)-N-phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N-(1-methylpropyl)-2,6-dinitrobenzenamine |
| cacodylic acid | hydroxydimethylarsine oxide |
| carbetamide | D-N-ethyllactamide carbanilate (ester) |
| CDAA | N—N-diallyl-2-chloroacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |
| cisanilide | cis-2,5-dimethyl-N-phenyl-1-pyrrolidinecarboxamide |
| CMA | calcium methanearsonate |
| cyanazine | 2-[[4-chloro-6-(ethylamino)-s-triazin-2-yl]amino]-2-methylpropionitrile |
| cycloate | S-ethyl N-ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |
| cyprazole | N-[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H-1,3,5-thiadiazine-2-thione |
| DCPA | dimethyl tetrachloroterephthalate |
| desmetryn | 2-(isopropylamino)-4-(methylamino)-6-methylthio)-s-triazine |
| diallate | S-(2,3-dichloroallyl)diisopropylthiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-dichlorophenoxy)phenoxy]propanoic acid |
| diethatyl | N-(chloroacetyl)-N-(2,6-diethylphenyl)glycine |
| difenzoquat | 1,2-dimethyl-3,5-diphenyl-1H-pyrazolium |
| dinitramine | $N^4,N^4$-diethyl-$\alpha,\alpha,\alpha$-trifluoro-3,5-dinitrotoluene-2,4-diamine |
| dinoseb | 2-sec-butyl-4,6-dinitrophenol |
| diphenamid | N,N-dimethyl-2,2-diphenylacetamide |
| dipropetryn | 2-(ethylthio)-4,6-bis(isopropylamino)-s-triazine |
| diquat | 6,7-dihydrodipyrido[1,2-a:2',1'-c]pyrazinediium ion |
| diuron | 3-(3,4-dichlorophenyl)-1,1-dimethylurea |
| DMSA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N-ethyl-N-(2-methyl-2-propenyl)-2,6-dinitro-4-(trifluoroethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenuron | 1,1-dimethyl-3-phenylurea |
| fenuron TCA | 1,1-dimethyl-3-phenylurea mono(trichloroacetate) |
| flamprop | N-benzoyl-N-(3-chloro-4-fluorophenyl)-DL-alanine |
| fluchloralin | N-(2-chloroethyl)-2,6-dinitro-N-propyl-4-(trifluoromethyl)aniline |
| fluometuron | 1,1-dimethyl-3-($\alpha,\alpha,\alpha$-trifluoro-m-tolyl)urea |
| fluorodifen | p-nitrophenyl $\alpha,\alpha$-trifluoro-2-nitro-p-tolyl ether |
| fluridone | 1-methyl-3-phenyl-5-[3-(trifluoromethyl)phenyl]-4(1H)-pyridinone |
| fosamine | ethyl hydrogen (aminocarbonyl)phosphonate |
| glyphosate | N-(phosphonomethyl)glycine and agriculturally suitable salts thereof |
| hexaflurate | potassium hexafluoroarsenate |
| hexazinone | 3-cyclohexyl-6-(dimethylamino)-1-methyl-1,3,5-triazin-2,4(1H,3H)-dione |
| ioxynil | 4-hydroxy-3,5-diiodobenzonitrile |
| isopropalin | 2,6-dinitro-N,N-dipropylcumidine |
| karbutilate | tert-butylcarbamic acid ester with 3-(m-hydroxyphenyl)-1,1-dimethylurea |
| lenacil | 3-cyclohexyl-6,7-dihydro-1H-cyclopentapyrimidine-2,4(3H,5H)-dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propionic acid |
| mefluidide | N-[(2,4-dimethyl-5-[[(trifluoromethyl)sulfonyl]amino]phenyl]-acetamide |
| methalpropalin | N-(2-methyl-2-propenyl)-2,6-dinitro-N-propyl-4-(trifluoromethyl)benzenamide |
| metham | sodium methyldithiocarbamate |
| methazole | 2-(3,4-dichlorophenyl)-4-methyl-1,2,4-oxadiazolidine-3,5-dione |
| metolachlor | 2-chloro-N-(2-ethyl-6-methylphenyl)-N-(2-methoxy-1-methylethyl)acetamide |
| metribuzin | 4-amino-6-tert-butyl-3-(methylthio)-as-triazin-5(4H)one |
| molinate | S-ethyl hexahydro-1H-azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| MSMA | monosodium methanearsonate |
| napropamide | 2-($\alpha$-naphthoxy)-N,N-diethylpropionamide |
| naptalam | N-1-naphthylphthalamic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichlorophenyl p-nitrophenyl ether |
| nitrofluorfen | 2-chloro-1-(4-nitrophenoxy)-4-(trifluoromethyl)benzene |
| norea | 3-(hexahydro-4,7-methanoindan-5-yl)-1,1-dimethylurea |
| norflurazon | 4-chloro-5-(methylamino)-2-($\alpha,\alpha,\alpha$-trifluoro-m-tolyl)-3(2H)-pyridazinone |
| oryzalin | 3,5-dinitro-$N^4,N^4$-dipropylsulfanilamide |
| oxadiazon | 2-tert-butyl-4-(2,4-dichloro-5-isopropoxyphenyl)$\Delta^2$-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| picloram | 4-amino-3,5,6-trichloropicolinic acid |
| procyazine | 2-[[4-chloro-6-(cyclopropylamino)-1,3,5-triazine-2-yl]amino]-2-methylpropanenitrile |

-continued

| Common Name | Chemical Name |
| --- | --- |
| profluralin | N-(cyclopropylmethyl)-α,α,α-trifluoro-2,6-dinitro-N-propyl-p-toluidine |
| prometon | 2,4-bis(isopropylamino)-6-methoxy-s-triazine |
| prometryn | 2,4-bis(isopropylamino)-6-(methylthio)-s-triazine |
| pronamide | 3,5-dichloro(N-1,1-dimethyl-2-propynyl)benzamide |
| propachlor | 2-chloro-N-isopropylacetanilide |
| propanil | 3',4'-dichloropropionalide |
| propazine | 2-chloro-4,6-bis(isopropylamino)-s-triazine |
| propham | isopropyl carbanilate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)-acetanilide |
| secbumeton | N-ethyl-6-methoxy-N'-(1-methylpropyl)-1,3,5-triazine-2,4-diamine |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| TCA | trichloroacetic acid and its salts |
| tebuthiuron | N-[5-(1,1-dimethylethyl)-1,3,4-thiadiazol-2-yl]N,N'-dimethylurea |
| terbacil | 3-tert-butyl-5-chloro-6-methyluracil |
| terbuchlor | N-(butoxymethyl)-2-chloro-N-[2-(1,1-dimethylethyl)-6-methylphenyl]acetamide |
| terbuthylazine | 2-(tert-butylamino)-4-chloro-6-ethylamino)-s-triazine |
| terbutol | 2,6-di-tert-butyl-p-tolyl methylcarbamate |
| terbutryn | 2-(tert-butylamino)-4-(ethylamino)-6-methylthio)-s-triazine |
| tetrafluron | N,N-dimethyl-N'-[3-(1,1,2,2-tetrafluoroethoxy)phenyl]urea |
| thiobencarb | S-[(4-chlorophenyl)methyl] diethylcarbamothioate |
| triallate | S-(2,3,3-trichloroallyl)diisopropylthiocarbamate |
| trifluralin | α,α,α-trifluoro-2,6-dinitro-N,N-dipropyl-p-toluidine |
| trimeturon | 1-(p-chlorophenyl)-2,3,3-trimethylpseudourea |
| 2,3,6-TBA | 2,3,6-trichlorobenzoic acid and agriculturally suitable salts and esters thereof |
| 2,4-D | (2,4-dichlorophenoxy)acetic acid and agriculturally suitable salts and esters thereof |
| 2,4-DB | 4-(2,4-dichlorophenoxy)butyric acid and agriculturally suitable salts and esters thereof |
| 2,4-DEP | tris[2-(2,4-dichlorophenoxy)-ethyl] phosphite |
| methabenzthiazuron | 1,3-dimethyl-3-(2-benzothiazolyl)-urea |
| chlortoluron | N'-(3-chloro-4-methylphenyl)-N'N-dimethylurea |
| isoproturon | N-(4-isopropylphenyl)-N'N'-dimethylurea |
| metoxuron | N'-(3-chloro-4-methoxyphenyl)-N,N-dimethylurea |

When an added herbicide is water-soluble, the pH of the resulting composition may need to be adjusted to lie within the range of 6 to 10. And further, water-soluble herbicides may act to replace, in part or in toto, the stabilizing inorganic and/or carboxylic acid salts.

The methods for making the stabilized compositions of this invention are well known and include ball-milling, bead-milling, sand-milling, colloidmilling and air-milling combined with high-speed blending.

A preferred technique for the preparation of stabilized compositions of Formula II involves suspending a compound of Formula I in water containing surfactants and thickening or suspending agents followed by neutralization with the desired base such as ammonium or sodium hydroxide to a pH of 6.0–10.0, preferably 7.0–9.0, followed by addition of the solid insolubilizing salt to the formulation with agitation. The technique of adding the insolubilizing salt is important. It is best to add the salt in increments to the neutralized conjugate acid in order to develop the precipitate more slowly; otherwise, a tacky solid or gum can form. The resulting suspension is then colloid-milled or bead-milled to a particle size of 1–20 microns, preferably 2–8 microns. The resulting stable aqueous suspension is suitable for use in herbicidal applications.

EXAMPLE 1

2-Chloro-N-[(4-methoxy-6-methyl-1,3,5-triazin-2-yl)aminocarbonyl]benzenesulfonamide: 34.20%
sodium alkylnaphthalenesulfonate: 2.00%
polysaccharide thickener: 0.05%
magnesium aluminum silicate thickener: 0.20%
diammonium hydrogen phosphate: 16.05%
ammonium hydroxide solution (29% NH$_3$): 5.60%
water and impurities: balance The sodium alkylnaphthalenesulfonate was dissolved in the water with stirring and the sulfonamide was added in increments and allowed to disperse well. To the dispersion was added the ammonium hydroxide to form the salt of the sulfonamide. The resulting pH was 7.5. Stirring was continued while the diammonium hydrogen phosphate was added and allowed to dissolve (28.5% of solution). The polysaccharide and silicate thickeners were added and the resulting mixture was ground in a sand-mill to produce particles essentially under five microns in size. The pH of the composition was 7.8. On accelerated aging at 45° C. for 3 weeks, the formulation did not settle appreciably and the suspended solids remained soft. The entire formulation could be easily fluidized by stirring or shaking. No detectible decomposition of active component occurred while a comparable composition containing no diammonium hydrogen phosphate showed 6% relative decomposition under the same conditions.

EXAMPLE 2

The following example illustrates an in situ preparation of a composition of a salt of Formula II from the conjugate acid of Formula I.

2-Chloro-N-[(4-methoxy-6-methyl-1,3,5-triazin-2-yl)aminocarbonyl]benzenesulfonamide: 33.9%
sodium ligninsulfonate: 2.0%
37.5% diammonium hydrogen phosphate solution: 64.1%

The sodium ligninsulfonate and sulfonamide were added with stirring to the phosphate solution. The mixture then was ground in a sand-mill to give particles of essentially less than five microns. The pH of the composition was 8.25. A sample aged for 2 weeks at 45° C. showed 0.47% relative decomposition of active component while a composition containing no phosphate showed 6.0% relative decomposition of the same component. No appreciable settling of the stabilized, aged composition was seen and it was easily fluidized with agitation.

EXAMPLE 3

A stable suspension of the ammonium salt of the sulfonylurea, 2-[[(4-Chloro-6-methoxypyrimidin-2-yl)aminocarbonyl]aminosulfonyl]benzoic acid, ethyl ester, was prepared as described in Example 2 using the same percentages of ingredients. The pH of the composition as 7.95. A sample aged for 2 weeks at 45° C. showed a 0.4% relative decomposition of active component while a composition without phosphate showed 4.0% relative decomposition of the same component. Settling of the aged composition was slight and it was readily fluidized with agitation.

EXAMPLE 4

2-[[(4-Methoxy-6-methyl-1,3,5-triazin-2-yl)aminocarbonyl]aminosulfonyl]benzoic acid, methyl ester: 21.3%
sodium ligninsulfonate: 1.11%
sodium hydroxide (50%): 4.48%
sodium acetate: 18.71%
polysaccharide thickener: 0.05%
water and impurities: balance With stirring, the sodium ligninsulfonate and sodium hydroxide were dissolved in the water and the sulfonylurea was added in portions and allowed to react to form the water-soluble sodium salt. To the solution was added one-fourth of the sodium acetate and, 5 minutes later, another one-fourth. The remainder of the sodium acetate was added after precipitation of the sulfonylurea salt was observed to be occurring rapidly, after about 15 minutes. The percentage of sodium acetate in the aqueous phase was 25.0. The resulting composition was ground in a sandmill to produce particles essentially under five microns in size. The polysaccharide thickener was added several minutes before completion of the milling operation. The pH of the composition was 9.03. On aging at 45° C. for 3 weeks, suspended solids did not settle and the formulation could be readily fluidized with shaking. No detectable decomposition of active ingredient occurred while a composition without acetate showed 30% decomposition over the same accelerated aging period.

In the following examples, stable suspensions of sulfonylureas are prepared as described in Example 4 using salts as stabilizers against chemical decomposition and to prevent crystal growth:

| Ex. | Sulfonylurea (neutral. agent) | Salt (% in $H_2O$) |
|---|---|---|
| 5 | A (NaOH) | sodium acetate (20) |
| 6 | B ($NH_4OH$) | ammonium acetate (30) |
| 7 | C (NaOH) | sodium thiocyanate (25) |

A = 2-[[(4,6-dimethylpyrimidin-2-yl)aminocarbonyl]aminosulfonyl]benzoic acid, methyl ester.
B = 2-[[(4,6-dimethoxypyrimidin-2-yl)aminocarbonyl]aminosulfonylmethyl]benzoic acid, methyl ester.
C = N-[(4,6-dimethylpyrimidin-2-yl)aminocarbonyl]2-hydroxybenzenesulfonamide, ethanesulfonate.

EXAMPLE 8

3-[[(4-Methoxy-6-methyl-1,3,5-triazin-2-yl)aminocarbonyl]aminosulfonyl]-2-thiophenecarboxylic acid, methyl ester: 12.0%
sodium alkylnaphthalenesulfonate: 2.4%
lithium hydroxide-$H_2O$: 1.3%
lithium acetate: 29.2%
water and impurities: remainder A stable suspension of the lithium salt of the sulfonylurea was prepared as described in Example 4. The lithium acetate concentration in the aqueous phase was 35%. The pH of the composition was 7.9. A sample aged at 45° C. for 3 weeks showed no loss of active ingredient while the loss of the same ingredient from a composition without lithium acetate aged in the same manner was over 20%.

EXAMPLE 9

The ammonium salt of the sulfonamide of Example 1 is air-milled to give a product with a particle size essentially less than five microns then dispersed with good agitation in a mixture of the remaining components of the formulation of Example 1. The suspension behavior and chemical stability are essentially as described in Example 1.

What is claimed is:

1. An aqueous composition having a pH in the range 6–10 and having improved chemical and suspension stability consisting essentially of an agriculturally suitable salt of a carboxylic or an inorganic acid, or mixtures of such carboxylic or inorganic acid salts, provided that the solubility of carboxylic or inorganic acid salts at 5° C. and at pH 6–10 is greater than or equal to 3% and further provided that the pH of a 0.1 molar solution of the carboxylic or inorganic acid salt is between 6 and 10, and one or more compounds selected from

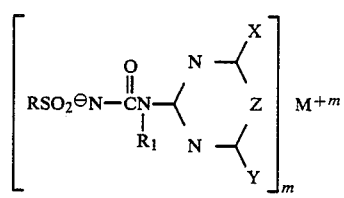

wherein the concentration of the carboxylic or inorganic acid salt or salts is between 3% and the salt saturation limit of the aqueous solution, and

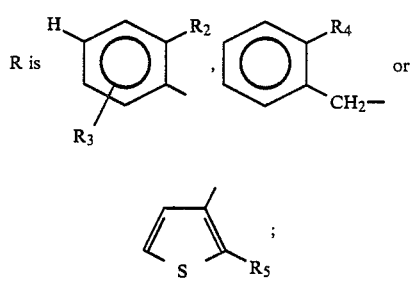

$R_1$ is H or $CH_3$;
$R_2$ is F, Cl, Br, $C_1$-$C_4$ alkyl, $SO_2NR_6R_7$, $S(O)_nR_8$, $SO_2NCH_3(OCH_3)$, $CO_2R_9$, $OSO_2R_{10}$, $OR_{11}$, $NO_2$,

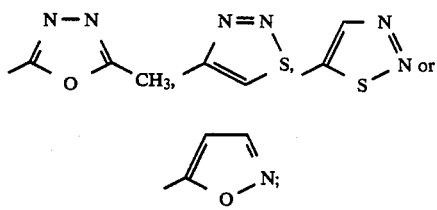

$R_3$ is H, F, Cl, Br, $CH_3$, $OCH_3$ or $CF_3$;
$R_4$ is Cl, $NO_2$ or $CO_2R_{10}$;
$R_5$ is Cl, Br, $SO_2NR_6R_7$, $S(O)_nR_{10}$ or $CO_2R_{10}$;
$R_6$ and $R_7$ are independently $C_1$–$C_3$ alkyl;
$R_8$ is $C_1$–$C_3$ alkyl or $C_1$–$C_3$ alkyl substituted by 1-5 atoms of F, Cl or Br;
$R_9$ is $C_1$–$C_4$ alkyl, $CH_2CH_2OCH_3$, $CH_2CH_2Cl$ or $CH_2CH=CH_2$;
$R_{10}$ is $C_1$–$C_3$ alkyl;
$R_{11}$ is $C_1$–$C_4$ alkyl, $CH_2CH=CH_2$, $CH_2C\equiv CH$, or $C_1$–$C_3$ alkyl substituted with 1-5 atoms of F, Cl or Br;
n is 0 or 2;
Z is CH or N;
X is $CH_3$, $OCH_3$, Cl or $OCHF_2$;
Y is $CH_3$, $OCH_3$, $CH(OCH_3)_2$, $OCHF_2$ or

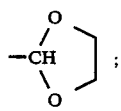

and
$M^{+m}$ is an agriculturally suitable cation;
m is 1, 2, or 3;
provided that when X is Cl then Z is CH and Y is $OCH_3$ or $OCF_2H$.

2. Compositions of claim 1 wherein the counterion of the carboxylic or inorganic acid salt is an ammonium, substituted ammonium or alkali metal ion and when the compound is a salt of Formula I, then M is also an ammonium, substituted ammonium or alkali metal ion.

3. Compositions of claim 2 wherein

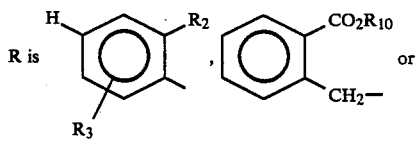

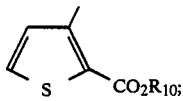

$R_1$ is H;
$R_2$ is Cl, $CH_3$, $SO_2N(CH_3)_2$, $S(O)_nR_8$, $CO_2R_9$, $OSO_2R_{10}$, $OR_{11}$ or $NO_2$;
$R_3$ is H, Cl, $CH_3$, $OCH_3$ or $CF_3$;
$R_8$ is $C_1$–$C_3$ alkyl, $CF_3$, $CF_2H$ or $CF_2CF_2H$;
$R_9$ is $C_1$–$C_4$ alkyl; and
$R_{11}$ is $C_1$–$C_4$ alkyl, $CF_3$, $CF_2H$ or $CF_2CF_2H$.

4. Compositions of claim 3 wherein the compound is an agriculturally suitable salt of Formula I.

5. Compositions of claim 4 wherein the cation of the compound of Formula I and the cation of the carboxylic or inorganic acid salt are identical.

6. Compositions of claim 1 wherein the concentration of the carboxylic or inorganic acid salt or salts is greater than 10% and less than 40% or the salt saturation limit of the solution.

7. Compositions of claim 2 wherein the concentration of the carboxylic or inorganic acid salt or salts is greater than 10% and less than 40% or the salt saturation limit of the solution.

8. Compositions of claim 3 wherein the concentration of the carboxylic or inorganic acid salt or salts is greater than 10% and less than 40% or the salt saturation limit of the solution.

9. Compositions of claim 4 wherein the concentration of the carboxylic or inorganic acid salt or salts is greater than 10% and less than 40% or the salt saturation limit of the solution.

10. Compositions of claim 5 wherein the concentration of the caboxylic or inorganic acid salt or salts is greater than 10% and less than 40% of the salt saturation limit of the solution.

11. Compositions of claim 1 wherein the salt or salts are selected from $C_1$–$C_3$ carboxylic acids and inorganic acid salts.

12. Compositions of claim 2 wherein the salt or salts are selected from $C_1$–$C_3$ carboxylic acids and inorganic acid salts.

13. Compositions of claim 3 wherein the salt or salts are selected from $C_1$–$C_3$ carboxylic acids and inorganic acid salts.

14. Compositions of claim 4 wherein the salt or salts are selected from $C_1$–$C_3$ carboxylic acids and inorganic acid salts.

15. Compositions of the claim 5 wherein the salt or salts are selected from $C_1$–$C_3$ carboxylic acids and inorganic acid salts.

16. The composition of claim 1 comprising 2-chloro-N-[(4-methoxy-6-methyl-1,3,5-triazin-2-yl)aminocarbonyl]benzenesulfonamide, ammonium salt with diammonium hydrogen phosphate.

17. The composition of claim 1 wherein the compound of Formula I is an agriculturally suitable salt of 2-[[(4-chloro-6-methoxypyrimidin-2-yl)aminocarbonaminosulfonyl]benzoic acid, ethyl ester.

18. The composition of claim 1 wherein the compound of Formula I is an agriculturally suitable salt of 2-[[(4-methoxy-6-methyl-1,3,5-triazin-2-yl)aminocarbonyl]aminosulfonyl]benzoic acid, methyl ester.

19. The composition of claim 1 wherein the compound of Formula I is an agriculturally suitable salt of N-[(4,6-dimethylpyrimidin-2-yl)aminocarbonyl]-2-hydroxybenzenesulfonamide, ethanesulfonate.

20. The composition of claim 1 wherein the compound of Formula I is an agriculturally suitable salt of 3-[[(4-methoxy-6-methyl-1,3,5-triazin-2-yl)aminocarbonyl]aminosulfonyl]-2-thiophenecarboxylic acid, methyl ester.

21. The composition of claim 1 wherein the compound of Formula I is an agriculturally suitable salt of 2-[(4,6-dimethylpyrimidin-2-yl)aminocarbonyl]aminosulfonyl)benzoic acid, methyl ester.

22. The composition of claim 1 wherein the compound of Formula I is an agriculturally suitable salt of 2-chloro-N-[(4-methoxy-6-methyl-1,3,5-triazin-2-yl)aminocarbonyl]benzenesulfonamide.

23. The composition of claim 1 wherein the compound of Formula I is an agriculturally suitable salt of 2-[[(4,6-dimethoxypyrimidin-2-yl)aminocarbonyl]aminosulfonylmethyl]benzoic acid, methyl ester.

24. The composition of claim 1 wherein the carboxylic or inorganic acid salt is selected from diammonium hydrogen phosphate, ammonium acetate, sodium acetate, lithium acetate, potassium acetate, or sodium thiocyanate.

25. The composition of claim 1 having a pH in the range 7–9.

* * * * *